United States Patent [19]
Fallet et al.

[11] Patent Number: 6,040,904
[45] Date of Patent: Mar. 21, 2000

[54] DIFFUSE OPTICAL TRANSMISSION DENSITY MEASUREMENT SYSTEM

[75] Inventors: Eric L. Fallet, Pittsford; Michael R. Goodwin, Rochester; Timothy P. Hahm, Spencerport, all of N.Y.

[73] Assignee: Eastman Kodak Company, Rochester, N.Y.

[21] Appl. No.: 09/219,691

[22] Filed: Dec. 23, 1998

[51] Int. Cl.[7] ........................................ G01J 1/04
[52] U.S. Cl. ........................... 356/236; 356/446; 250/228
[58] Field of Search .................................... 356/443, 446, 356/236; 250/228

[56] References Cited

U.S. PATENT DOCUMENTS

| | | | |
|---|---|---|---|
| 4,120,582 | 10/1978 | DeVries et al. | 356/73 |
| 4,310,249 | 1/1982 | Kramer | 356/414 |
| 4,688,943 | 8/1987 | Modarress | 356/436 |
| 4,900,923 | 2/1990 | Gerlinger | 250/228 |
| 4,919,535 | 4/1990 | Hohberg et al. | 356/429 |
| 4,937,764 | 6/1990 | Komatsu et al. | 702/137 |
| 4,963,027 | 10/1990 | Koizumi et al. | 356/416 |
| 5,243,409 | 9/1993 | Sagner | 356/436 |
| 5,636,633 | 6/1997 | Messerschmidt et al. | 128/633 |
| 5,661,556 | 8/1997 | Schiff et al. | 356/236 |

*Primary Examiner*—Frank G. Font
*Assistant Examiner*—Layla Lauchman
*Attorney, Agent, or Firm*—Mark G. Bocchetti

[57] ABSTRACT

An apparatus for measuring diffuse optical transmission density of a photographic films sample uses two integrating spheres and a diffuse light source. Light from the light source is transmitted through a first light modulation system into the first integrating sphere. Light from the first integrating sphere is transmitted through a second light modulation system into the second integrating sphere. A fixed monochromator receives light at an exit port of the second integrating sphere. The light modulation systems take the form of adjustable diaphragms which allow for the modulation of the uniform radiance area located between the two integrating spheres and maintains the geometric and spectral conditions relating to the illumination of the sample located at the output port of the second integrating sphere.

11 Claims, 4 Drawing Sheets

DIFFUSE OPTICAL TRANSMISSION DENSITY MEASUREMENT SYSTEM

FIELD OF THE INVENTION

The present invention relates generally to optical inspection methods and apparatus and, more particularly, apparatus and methods for measuring diffuse optical transmission density of photographic film.

BACKGROUND OF THE INVENTION

In the manufacture and processing of photographic products, diffuse optical transmission density is one of the most important measurements used to characterize the film's properties. The apparatus used to make this measurement are typically referred to as densitometers. A variety of densitometers are known in the prior art. One common feature of many of these densitometers is that the optical density is determined based on calibration and adjustment of the linearity of the detector system. For such densitometers, this calibration must rely on some independent method or reference. Another way to measure diffuse optical transmission density is to determine the optical density with an approximation of the inverse square law. However, a disadvantage of this particular device is that it includes a large mechanical moving system for the light source or the detector which creates an optical instability. Devices are also known to approximate spectral specifications (for example, specifications of ISO 5-3) with one or several appropriate filters. Approximation of such spectral specifications by use of filters introduces error in the measurement result. This error is smaller for samples with spectrally flat transmittance than for samples without spectrally flat transmittance.

U.S. Pat. No. 4,937,764 to Komatsu et al teaches a calibrated densitometer and a method of calibration. A lamp is energized for a predetermined duration of time to illuminate a standard density plate with a spot light formed by a bottom opening of a light tight barrel through an aperture of a transparent plate. The light reflected by the subject sample passes through a measuring aperture and the light tight barrel and reaches a light receiving element through a lens and filter. The light receiving element provides an output corresponding to an intensity of the light received.

U.S. Pat. No. 5,661,556 to Schiff et al teaches a system that measures total integrated scatter from a surface using two integrating devices which can both be integrating spheres or one can be a integrating sphere and the other can be a mirror or lens. This system includes a light source and source optics which direct a beam of light toward the surface. The first integrating device is positioned and configured to receive a first portion of the scattered light which corresponds to a first range of spatial frequencies. The second integrating device is positioned and configured to receive a second portion of the scattered light corresponding to a second range of spatial frequencies. Total integrated scatter data is generated for each range of spatial frequencies and is used to approximate the spectral scatter function of the surface. RMS roughness is then approximated for any range of spatial frequencies.

U.S. Pat. No. 4,900,923 to Gerlinger teaches a reflectance measuring apparatus having a predetermined aperture for the receiving optic. A light-conducting device arranged between the measuring aperture and the specimen enlarges the effective measuring surface of the specimen so that even specimens having a large surface structure can be measured.

U.S. Pat. No. 4,120,582 to DeVries et al teaches an apparatus for testing an optical element sample such as a mirror for determining both the total amount of light reflected from and the total amount of light transmitted by a predetermined area of that optical element sample. The apparatus includes a pair of axially aligned light-integrating spheres between which is clamped the test sample so that no light enters or escapes from either sphere. A substantially collimated beam of light is directed through one sphere against the test sample at an angle to the sphere axis. Silicon photovoltaic light sensitive detectors connected to amplified readout units indicate the total light reflectivity in one sphere and the total light transmission to the other sphere.

Those densitometers of the prior art which do not require independent calibration of the detector linearity are lacking in the ability to determine the diffuse optical transmission density of a sample with a high degree of measuring repeatability and reproducibility. In other words, measuring the same sample on the same apparatus will often result in different measurements for the diffuse optical transmission density of that sample. Further, measuring one sample on two distinct but identical apparatus will also often result in two different diffuse optical transmission densities for that same sample.

SUMMARY OF THE INVENTION

It is therefore an object of the present invention to provide an apparatus for measuring diffuse optical transmission density of photographic films which measures such characteristics of the film with a high degree of measuring repeatability and reproducibility without independent calibration and adjustment of the linearity of the detector system.

It is a further object of the present invention to provide a densitometer based on the optical inverse square law which does not require a system for moving the light source or the detector.

Briefly stated, the foregoing and numerous other features, objects and advantages of the present invention will become readily apparent upon a reading of the detailed description, claims and drawings set forth herein. These features, objects and advantages of the present invention are accomplished by using a first integrating sphere to modify a light source (as used herein, "light" means any form of electromagnetic radiation, whether visible or invisible to the human observer) to thereby produce an area of uniform radiance at its output port, a second integrating sphere with an input port which permits collection of radiant flux from the uniform radiance area through an adjustable diaphragm between the two integrating spheres. The adjustable diaphragm allows for the modulation of the uniform radiance area located between the two integrating spheres and maintains the geometric and spectral conditions of the illumination of the sample located at the output port of the second integrating sphere. The adjustable diaphragm preferably takes the form of two motor driven flat knives or blades which can be driven toward or away from one another to vary the uniform radiance area of the aperture between the output port of the first integrating sphere and the input port of the second integrating sphere. Light which exits the output port of the second integrating sphere is collected and measured by a spectral detector system.

DETAILED DESCRIPTION OF THE INVENTION

Figure 1:
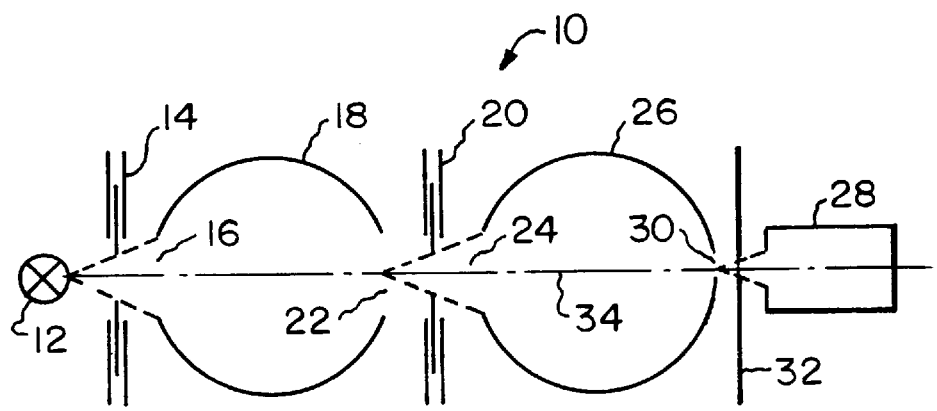
FIG. 1 is a simple top plan view schematic of the apparatus of the present invention.

Turning first to FIG. 1, there is shown a schematic representation of the apparatus 10 of the present invention. Light from a spectrally and geometrically appropriate source 12 (for example, meeting the spectral requirements of ISO 5-3 and meeting the geometrical requirements of ISO 5-2) is collected through a first a variable aperture or light modulation system 14 at the entrance port 16 of a first integrating sphere 18. There is a second variable aperture or light modulation system 20 positioned at the exit port 22 of the first integrating sphere 18. This second variable aperture 20 is used to modulate the light from exit port 22 of the first integrating sphere 18 to the entrance port 24 of the second integrating sphere 26. There is a spectrally and geometrically appropriate detector system 28 which receives light from the exit port 30 of the second integrating sphere 26. A sample 32 to be analyzed is placed between exit port 30 and detector system 28. Through the adjustment of the first and second variable apertures 14, 20, measurement of the optical transmission density of the sample 32 can be performed which conforms to the spectral and geometrical requirements for the particular measurement of interest (for example, the requirements of ISO 5-2 and ISO 5-3).

Without a sample 32 on the optical axis 34 and for a first position of the first variable aperture 14 (and therefore a known area), the quantity of light corresponding to the reference uniform radiance area A of the second variable aperture 20, is measured with the spectral detector system 28 using computer software appropriate to the spectral range and result of interest. After such first measurement is taken, a sample 32 is placed on the optical axis 34 between exit port 30 and spectral detector system 28. The second variable aperture 20 and/or the first variable aperture 14 are then opened to achieve the same quantity of light received by the spectral detector system 28 when sample 32 was not present. The new uniform radiance area B of the second variable aperture 20 is then measured. With these measurements made, the microprocessor (not shown) can calculate the diffuse optical transmission density D of the sample 32 with the formula:

$$D = \log_{10}[B/A]$$

Figure 2:
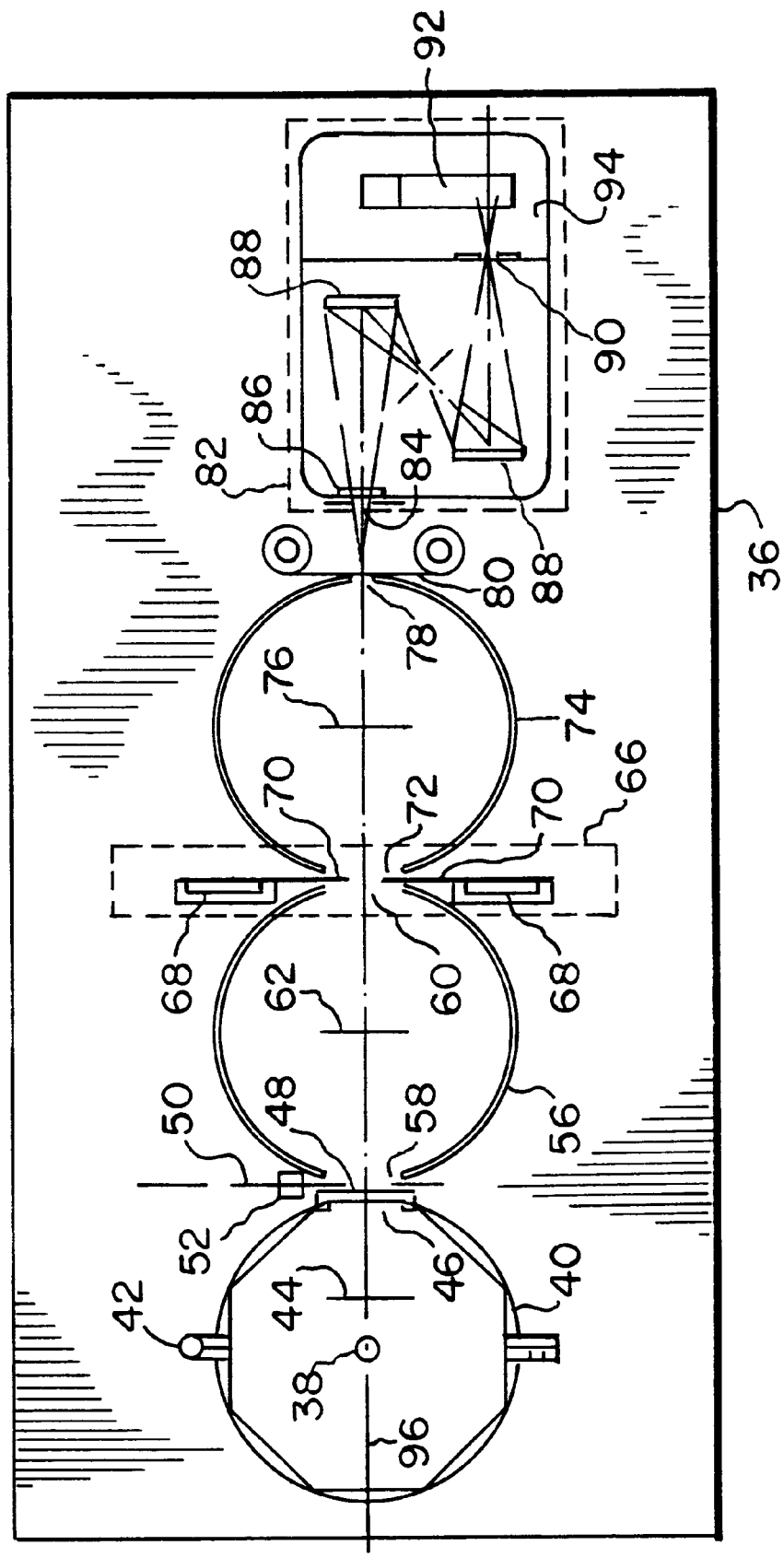
FIG. 2 is a more detailed plan view schematic of the apparatus of the present invention.

Looking next at FIG. 2 there is shown a top plan view schematic of an exemplary apparatus 10 of the present invention shown in greater detail than that depicted in FIG. 1. The apparatus 10 is fixed on an optical table 36 which is supported by floor stabilizer vibration isolator (not shown). There is a lamp 38 (FEL 1000W) inside a spherical lamp housing 40 which has a diameter of 500 mm. Lamp housing 40 includes an interior access system 42 which permits access for lamp replacement and alignment. Lamp housing 40 collects all the energy from lamp 38 with lamp 38 having good stability (varying less than 0.1% per hour). There is a baffle 44 located between lamp 38 and the exit port 46 of lamp housing 40. The diameter of exit port 46 is 125 mm. Baffle 44 and the interior walls of lamp housing 40 are coated with a diffusing, spectrally white reflectance material to provide a uniform radiance area with a high light efficiency. A heat absorbing filter 48 with an appropriate thickness (for example, 7 mm thick Hoya HA-50 filter for a distribution temperature of 3050 kelvins) is fixed on the exit port 46 of lamp housing 40. In this example, this heat absorbing filter 48 gives the spectral characteristics required by ISO 5-3 for the measurement of the diffuse optical transmission density.

Figure 3:
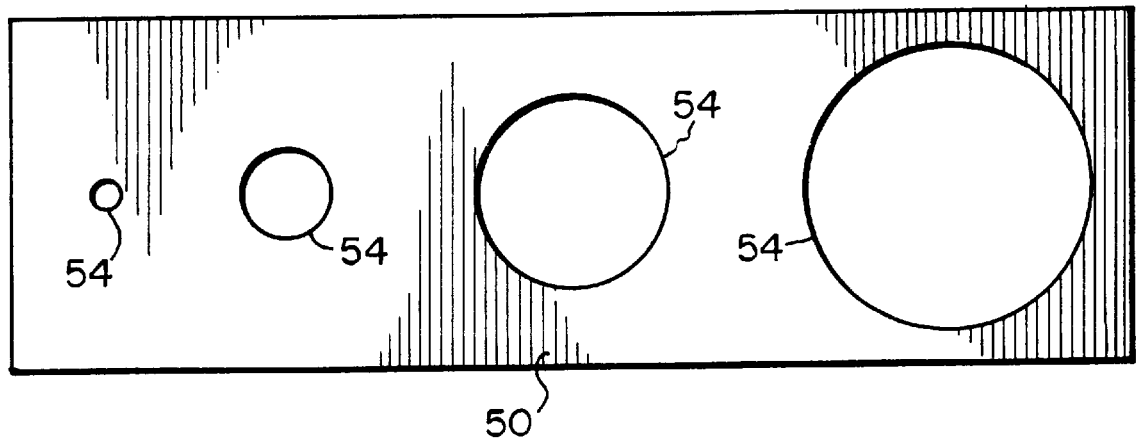
FIG. 3 is a plan view of the first aperture plate.

Located adjacent to heat absorbing filter 48 is a first aperture plate 50. First aperture plate 50 is mounted to a linear slide mechanism 52 driven by a motor (not shown). As shown in FIG. 3, first aperture plate 50 includes a series of orifices 54 of differing diameters. With such a moveable aperture plate, one orifice or another may be positioned on the optical axis so as to permit more or less light to be transmitted into the first integrating sphere 56 (as shown in FIG. 2). The areas of the orifices vary from one to another in such a way as to make an appropriate area progression from orifice to orifice. This area progression is made in such a way that the ratios of the areas of adjacent orifices are approximately constant. That is, for example, if the area of the second orifice is 100 times the area of the first orifice, then the area of the third orifice should be 100 times the area of the second orifice, the area of the fourth orifice should be 100 times the area of the third orifice, etc. The exact ratio of areas (in this example 100:1) is dependent on the ratio of the extreme and finite areas permitted by the light modulation system 66. In order to avoid influencing the spectral product, the reflectance of the first aperture plate 50 should be spectrally non-selective and its total reflectance lower than 5%. This may be accomplished by covering the first aperture plate with an appropriate flat black coating. (The spectral product is the mathematical product of the spectral characteristic, wavelength by wavelength, of all components of the measuring system.)

Still referring to FIG. 2 as depicting an exemplary apparatus 10, there is shown a first integrating sphere 56 having a diameter of 500 mm. The entrance port 58 and the exit port 60 of first integrating sphere 56 both have a diameter of 125 mm. The first integrating sphere 56 collects light through the selected orifice 54 of first aperture plate 50 (both shown in FIG. 3). First integrating sphere 56 may include a central baffle 62 in order to provide a uniform radiance area at the exit port 60 such that variation in radiance across the uniform radiance area is less than 0.1%. A flat spectrally non-selective white reflectance material should be coated on the wall of the first integrating sphere 56 and baffle 62 in order to provide a high reflectance and thus high light throughput.

Positioned adjacent to exit port 60 is the light modulation system 66. Light modulation system 66 includes two motorized linear slide mechanisms 68 with a flat knife or blade 70 mounted to each of the motorized linear slide mechanisms 68. In such manner, the motorized linear slide mechanisms 68 can drive blades 70 toward and away from each other to vary the area through which light can be transmitted through exit port 60 into entrance port 72 of second integrating sphere 74. The uniform radiance area should be at least as large as the maximum area achievable through movement of blades 70 away from each other to allow light to be transmitted through exit port 60. The light modulation system 66, located between the exit port 60 of the first integrating sphere and the entrance port 72 of the second integrating sphere, permits the user of the apparatus 10 of the present invention to measure the uniform radiance area. Referring now to FIG. 2, flat knife 70 should be coated with an appropriate flat black coating. This flat black coating will not significantly influence the spectral product of the entire system. The light which passes through the uniform radiance area is collected in the second integrating sphere 74 which also has a diameter of 500 mm. The entrance port 72 of the second integrating sphere 74 has a diameter of 125 mm. There is a central baffle 76 within second integrating sphere 74. The exit port 78 of second integrating sphere 74 in this example has a diameter of 5 mm. Sample 80 is illuminated by exit port 78 with the sample 80 being placed in contact with the circumferential edge of exit port 78.

A detector system, preferably a double monochromator 82 with a subtractive configuration is positioned adjacent to sample 80. One may choose to use some device or means, other than a double monochromator, to achieve the spectral product for the measurement of interest. Examples include a single monochromator or glass or gelatin filters. Other devices to achieve this are well-known to those skilled in the art. Double monochromator 82 includes a slit 84 which receives light transmitted through exit port 78 and film sample 80. Entrance slit 84 is positioned at an appropriate solid angle (for example, the solid angle required by ISO 5-2 is equal to or less than ±10 degrees). Positioned behind slit 84 is a second order filter 86. Also mounted within the double monochromator 82 are two aberration corrected concave holographic gratings 88. Second order filter 86 and gratings 88 give an appropriate band pass value (for example, the band pass required by ISO 5-3 is 10 nm) with a negligible level of stray light over the entire wavelength range of interest and with acceptable uniformity of light passing through exit slit 90. Double monochromator 82 further includes a light detector, preferably a photomultiplier 92 located within a cooling chamber 94 which receives all of the light collected from exit port 78 and measures a quantity of light which passes through exit slit 90 of the double monochromator 82.

In the operation of the apparatus and method of the present invention, and with reference to FIG. 2, density is determined by calculating the base 10 logarithm of the ratio of two measured uniform radiance areas, namely the sample uniform radiance area and the reference uniform radiance area. To find the reference uniform radiance area, with no sample 80 positioned adjacent to exit port 78, linear slide mechanism 52 is actuated to position first aperture plate 50 such that a predetermined orifice 54 (shown in FIG. 3) is placed in alignment with optical axis 96. The size of the orifice 54 selected should be the largest orifice which will allow measurement of the highest density of the sample by subsequently increasing the area of either the second variable aperture alone or by increasing the areas of both the second variable aperture and the orifice 54. Motorized linear slide mechanism 68 is then actuated to adjust the position of blades 70 such that the second variable aperture created therebetween has a relatively small area. This small area of the second variable aperture should be the largest area which will allow measurement of the highest density of the sample by subsequently increasing the area of either the second variable aperture alone or by increasing the areas of both the second variable aperture and the orifice 54. The computer control system then determines the reference area A of the second variable aperture, that is the area between blades 70 which is also overlapped by exit port 60. Simultaneously, the quantity of light for each wavelength transmitted by the double monochromator 82 is measured by the photomultiplier. Once the reference measurement has been made, the sample uniform radiance area is determined as follows. A sample 80 is placed in position at exit port 78 and the computer control system causes the motorized linear slide mechanism 68 to increase the area of the second variable aperture. The area of the second variable aperture is increased to the point such that the same quantity of light (over a predetermined portion of the spectrum) as the reference measurement (that is, the measurement taken with no sample 80 in place) is received by the double monochromator 82. When the same quantity of light is being received by the double monochromator 82 as that which it received during the reference measurement, the computer control system can determine the new area B of the second variable aperture. The computer system can then calculate the density as the base 10 logarithm of the ratio of the area B and the area A. If the second variable aperture can not be set with an area such that the quantity of light received by the monochromator 82 with sample 80 in place is the same as received for the reference measurement, then after a larger orifice 54 is selected, the density of the sample can be measured relative to the sample whose density was just previously measured.

Figure 4:
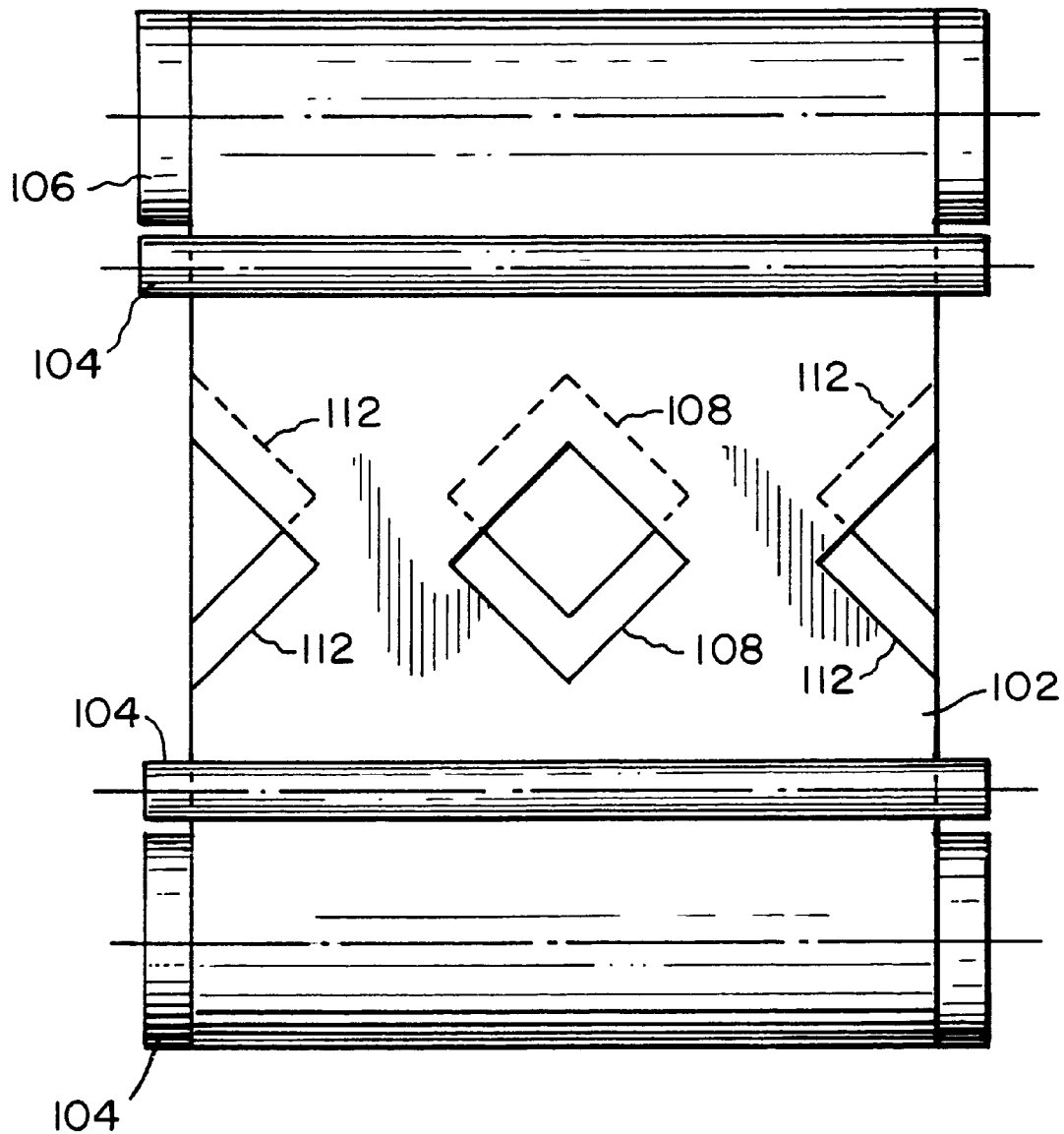
FIG. 4 is a front elevational view of an alternative second light modulation system.
Figure 5:
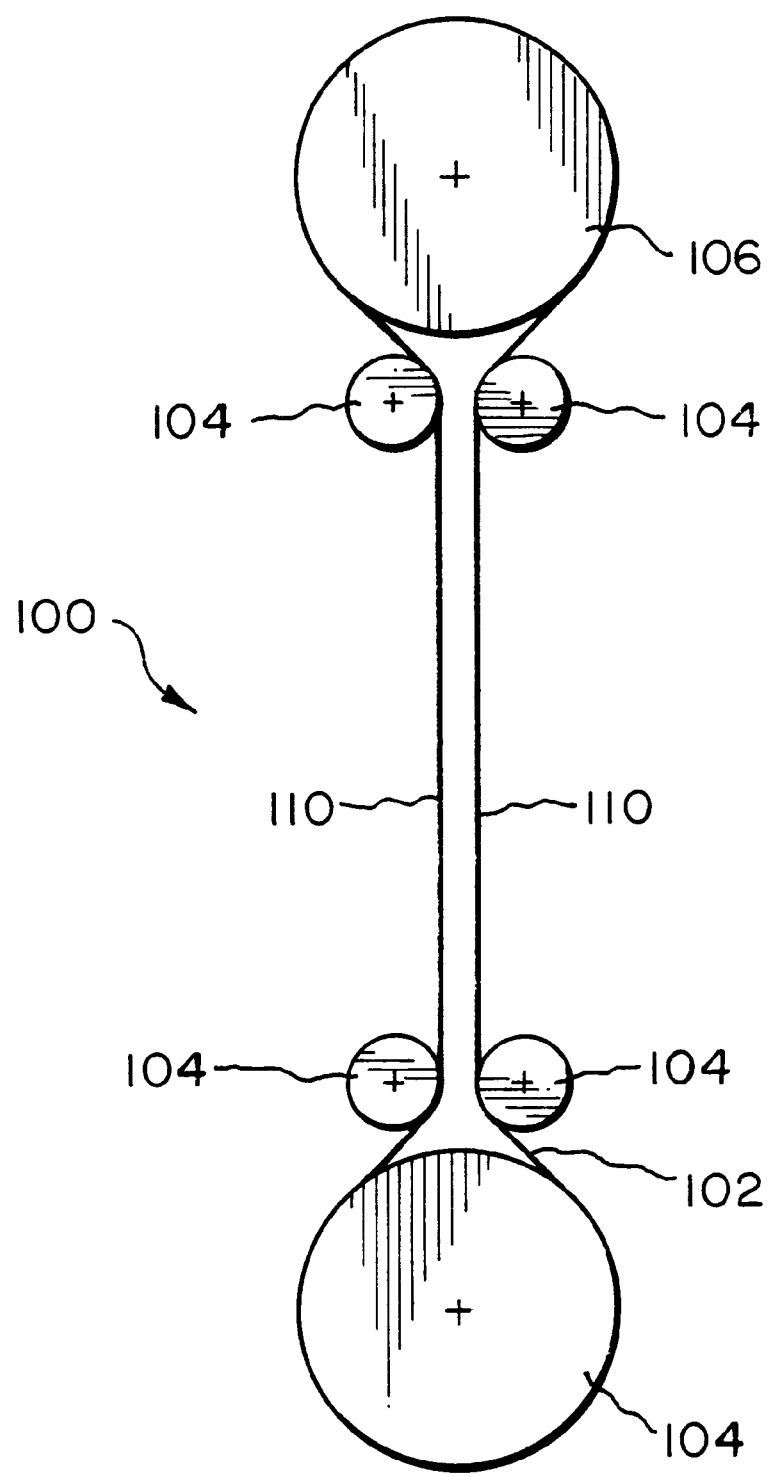
FIG. 5 is a side elevational view of the second light modulation system shown in 4.

Looking next at FIGS. 4 and 5, there is shown an alternative light modulation system 100 which includes a continuous belt 102 wrapped in a serpentine path about a series of five guide rollers 104 and a drive roller 106. Continuous belt 102 should be made from a flexible sheet of inelastic material. There are a pair of apertures 108 in belt 102. Apertures 108 are preferably square and oriented such that the area of overlap between apertures 108 remains square during movement of belt 102. Alternative light modulation system 100 is preferably designed such that zero slippage between drive roller 106 and belt 102 is maintained. Apertures 108, which reside in parallel segments 110 of continuous belt 102, are moved in opposite directions of equal magnitude by operation of the drive roller 106. The direction of movement of apertures 108 is orthogonal to the optical axis. In such manner, overlap of apertures 108 can be controllably varied. Cut-outs 112 in belt 102 are preferably provided adjacent apertures 108 for the purpose of aiding in the maintenance of planarity of parallel segments 110.

From the foregoing, it will be seen that this invention is one well adapted to obtain all of the ends and objects here in above set forth together with other advantages which are apparent and which are inherent to the invention.

It will be understood that certain features and subcombinations are of utility and may be employed with reference to other features and subcombinations. This is contemplated by and is within the scope of the claims.

As many possible embodiments may be made of the invention without departing from the scope thereof, it is to be understood that all matter herein set forth and shown in the accompanying drawings is to be interpreted as illustrative and not a limiting sense.

PARTS LIST 10 apparatus
12 light source
14 first variable aperture
16 entrance port
18 first integrating sphere
20 second variable aperture
22 exit port
24 entrance port
26 second integrating sphere
28 detector system
30 exit port
32 sample
34 optical axis
36 table
38 lamp
40 lamp housing
42 interior access system 44 baffle
46 exit port
48 heat absorbing filter
50 first aperture plate
52 linear slide mechanism
54 holes, orifices
56 first integrating sphere
58 entrance port
60 exit port
62 baffle
66 light modulation system
68 motorized linear slide mechanism
70 flat knives/blades
72 entrance port
74 second integrating sphere
76 baffle
78 exit port
80 sample
82 double monochromator
84 slit
86 second order filter
88 gratings
90 exit slit
92 photomultiplier
94 cooling chamber
96 optical axis
100 alternative light modulation system
102 continuous belt
104 guide rollers
106 drive roller
108 apertures
110 parallel segments
112 cut-outs

What is claimed is:

1. An apparatus for measuring diffuse optical transmission density of a film sample comprising:
   (a) a diffuse light source:
   (b) a first light modulation system through which light from said light source is transmitted to a first optical diffuser;
   (c) a second light modulation system positioned between said first optical diffuser and a second optical diffuser;
   (d) a detector system which receives light from an exit port of said second optical diffuser and through said second light modulation system; and
   (e) means for supporting the film sample between said exit port of said second optical diffuser and said detector system.

2. An apparatus as recited in claim 1 wherein:
said first optical diffuser is a first integrating sphere.

3. An apparatus as recited in claim 2 wherein:
said second optical diffuser is a second integrating sphere.

4. An apparatus as recited in claim 1 wherein:
said first light modulation system includes means for varying the size of a first aperture between said light source and said first optical diffuser.

5. An apparatus as recited in claim 1 wherein:
said second light modulation system includes means for varying the size of a second aperture between said first optical diffuser and second optical diffuser.

6. An apparatus as recited in claim 1 wherein:
said detector system is a fixed monochromator.

7. An apparatus as recited in claim 1 wherein:
said detector system is a double monochromator.

8. An apparatus as recited in claim 1 wherein:
said detector system is a single monochromator.

9. An apparatus as recited in claim 1 wherein:
said detector system is a filter.

10. An apparatus as recited in claim 1, said second light modulation system comprising:
   (a) a continuous belt having two aperture therethrough;
   (b) at least one guide roller; and
   (c) a drive roller, said continuous belt wrapped about said at least one guide roller and said drive roller such that said continuous belt follows a path which includes a pair of parallel segments, said two apertures residing in said parallel segments, said two apertures being movable through operation of said drive roller to vary an amount of overlap of said two apertures.

11. An apparatus as recited in claim 3, said second light modulation system comprising:
   (a) a continuous belt having two aperture therethrough;
   (b) at least one guide roller; and
   (c) a drive roller, said continuous belt wrapped about said at least one guide roller and said drive roller such that said continuous belt follows a path which includes a pair of parallel segments, said two apertures residing in said parallel segments, said two apertures being movable through operation of said drive roller to vary an amount of overlap of said two apertures.

* * * * *